(12) United States Patent
Khandelwal

(10) Patent No.: US 9,830,475 B2
(45) Date of Patent: Nov. 28, 2017

(54) INTEGRATED COLLABORATION PLATFORM FOR CONTEXTUAL COMMUNICATION

(71) Applicant: Sweet60online, Inc., Fremont, CA (US)

(72) Inventor: Anupam Khandelwal, Rajasthan (IN)

(73) Assignee: SageSurfer Inc., Fremont, CA (US)

( * ) Notice: Subject to any disclaimer, the term of this patent is extended or adjusted under 35 U.S.C. 154(b) by 125 days.

(21) Appl. No.: 14/800,510

(22) Filed: Jul. 15, 2015

(65) Prior Publication Data

US 2016/0019402 A1 Jan. 21, 2016

Related U.S. Application Data

(60) Provisional application No. 61/999,060, filed on Jul. 15, 2014.

(51) Int. Cl.
| | |
|---|---|
| G06F 21/62 | (2013.01) |
| G06F 19/00 | (2011.01) |
| H04L 29/06 | (2006.01) |
| H04L 12/58 | (2006.01) |
| H04L 29/08 | (2006.01) |

(52) U.S. Cl.
CPC ........ G06F 21/6254 (2013.01); G06F 19/322 (2013.01); H04L 51/32 (2013.01); H04L 63/0421 (2013.01); H04L 63/20 (2013.01); H04L 67/306 (2013.01)

(58) Field of Classification Search
CPC ........ G06F 17/30; G06F 21/00; G06F 19/322; G06Q 50/22; G06Q 10/10
See application file for complete search history.

(56) References Cited

U.S. PATENT DOCUMENTS

| | | | | |
|---|---|---|---|---|
| 7,590,547 | B2 * | 9/2009 | Lagadec | G06Q 30/02 705/307 |
| 2006/0265453 | A1 * | 11/2006 | Kaminsky | G06Q 10/107 709/206 |
| 2008/0077675 | A1 * | 3/2008 | Graef | G06Q 10/107 709/206 |
| 2011/0302249 | A1 * | 12/2011 | Orr | G06Q 10/107 709/206 |
| 2013/0138946 | A1 * | 5/2013 | Ayrapetian | H04L 63/0428 713/150 |
| 2013/0212190 | A1 * | 8/2013 | Patil | G06F 17/276 709/206 |
| 2015/0073828 | A1 * | 3/2015 | Mortara | G06F 19/3487 705/3 |

* cited by examiner

*Primary Examiner* — Minh Dinh
*Assistant Examiner* — Paul Callahan

(57) ABSTRACT

An integrated collaboration platform with various communication and collaboration tools includes an analytic engine to perform communication and mood analysis of conversations among other analyses. The platform enables a method for contextual communication, in an embodiment. The method for contextual communication involves receiving an indication of sending a message from a sender to a recipient, understanding the topic of the message, analyzing various parameters associated with the sender and the recipient, and suggesting a list of messages, information, alternate communication channels, desired moods for the receiver at the time of receiving the message, and timing of delivery of the message for a desired response from the recipient.

23 Claims, 9 Drawing Sheets

300

400

Documents:
  Crisis Plan
  Strength & Success
  Education Plan

Chat History:
  <user1> How are you feeling now?
  <consumer1> Not feeling good. Don't feel like taking medication?
  <user1> I spoke to your teacher the other day. She was really impressed by your progress in Mathematics.

To: _____

Topic: _____  Category [Consumer State ▷]

Tag: Consumer ✖ Anxiety ✖

INTEGRATED COLLABORATION PLATFORM FOR CONTEXTUAL COMMUNICATION

This application claims the benefit of U.S. Provisional Application No. 61/999,060, filed Jul. 15, 2014.

TECHNICAL FIELD

The embodiments herein relate to contextual communication and, more particularly, to contextual communication using an integrated collaboration platform.

BACKGROUND

With the ever increasing penetration of Internet and Telecommunications all over the world, there has been a proliferation of various communication tools and platforms. However, collaboration and communication between people is still happening in silos and it is hard to maintain context between various communications that might happen over different communication channels.

Collaboration platforms available today are mostly targeted in nature such as WORDPRESS for blogging, GOOGLE TALK or YAHOO MESSENGER for instant messaging chat, OUTLOOK/GMAIL/YAHOO MAIL for email, YAHOO ANSWERS for Question and Answers, DROPBOX or GOOGLE DRIVE for cloud storage and collaborative document editing, FACEBOOK/TWITTER for social communication, and so on.

The prevalence of the vast array of communication mechanisms may be explained by different needs for a same individual for different purposes (personal, official, document collaboration, secure communication, group communication, and so on), and variations in preferences between individuals. For example, some people prefer instant messaging over waiting for email. And, some others may voice/video chat over instant messaging and so on.

More and more industries are now relying on online communication tools for collaboration and service delivery. The various communication channels provide an option for individuals to choose the right channel suitable to their needs and preferences. And, typically, one individual engages with multiple forms of communication over a period of time due to their own changing needs and the preferences of other individuals they communicate with. The diverse nature of communications makes it difficult to maintain context across channels due to the discrete nature of the communication channels available today.

In certain industries, having a contextual conversation every time is important to the success or failure of systems. For example, let us consider a health care services delivery platform for directed to mental health, substance abuse, or disability services pertaining to the Healthcare industry. For online communication platforms to succeed in such a scenario requires, care givers and individuals being able to communicate with each other well over long periods of time. And, as with many systems, health care systems can be dynamic. Care givers can change and move to new jobs, and different care givers attend to different needs of a care receiving individual and so on. And, therefore, a care receiving individual may be interacting with many different care givers. In such a dynamic environment, it is impossible to maintain context of conversation with discrete communication and collaboration tools available today.

BRIEF DESCRIPTION OF THE FIGURES

The embodiments herein will be better understood from the following detailed description with reference to the drawings, in which:

FIG. 8 and FIG. 9 show a message composing screen, according to various embodiments herein.

DETAILED DESCRIPTION OF EMBODIMENTS

Figure 1:
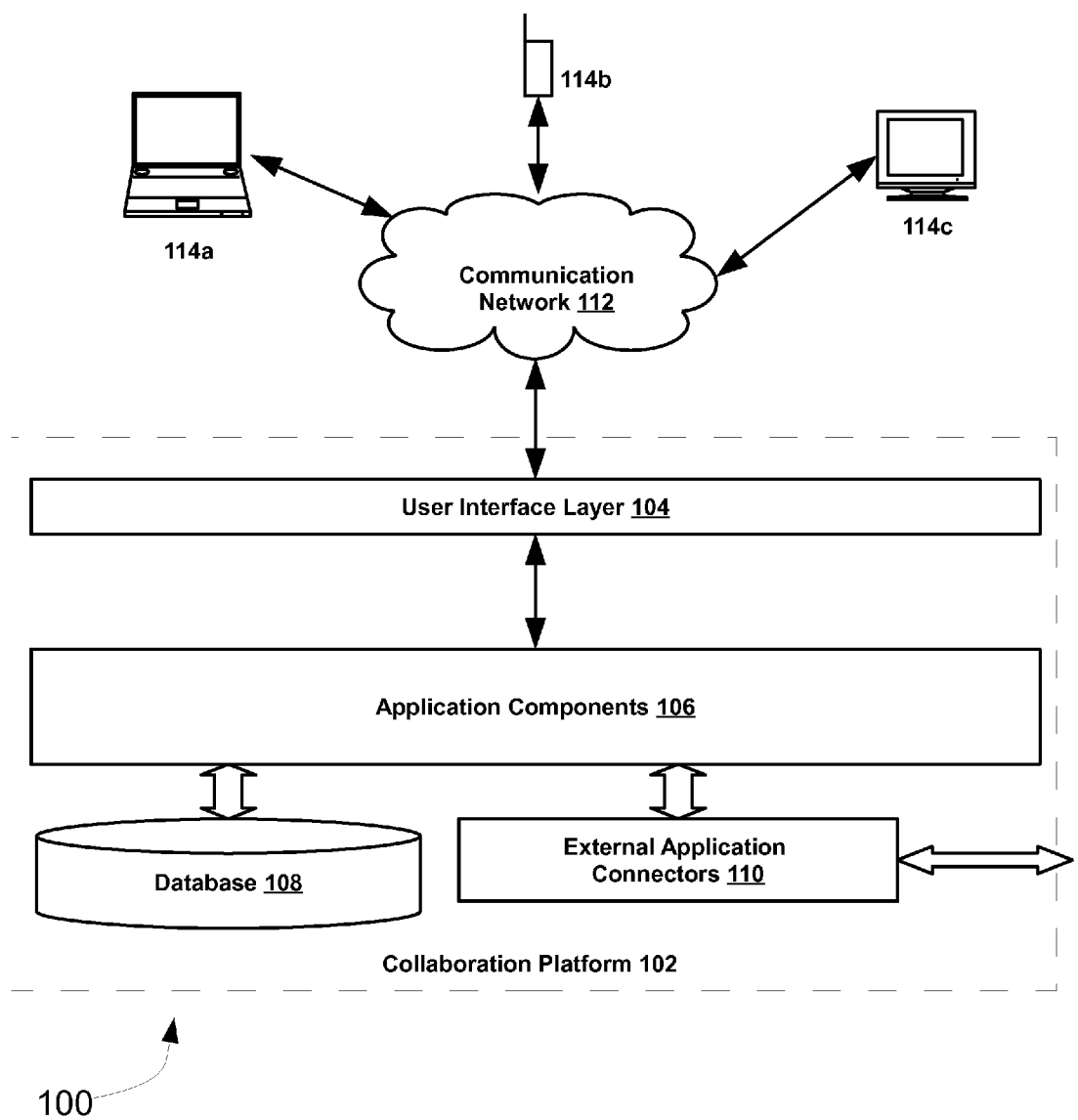
FIG. 1 illustrates a the collaboration platform accessible in a network environment, according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein disclose an integrated collaboration platform and associated methods and systems for contextual communication. Examples are based on a care and coordination platform for delivering health care services as the context. Systems and methods disclosed herein may be applied to delivering services through a under system of care deployment for Mental Health, Substance Abuse, Disability, and patients of HIV and other diseases in underserved population and/or rich or developing economies together with processes around life sciences, providing patient care through collaboration between Healthcare providers, Insurance Providers, Health and Human Service Agencies, Accountable Care organization, Primary Care Networks, Patient Centered Medical Homes Researches, Senior living organizations, Community organization to name a few.

It will be evident to an ordinarily skilled person in the field that systems and methods disclosed herein can be applied to enable collaboration and communication for service delivery in other industry verticals as well. Such collaboration and communication enabled by the methods and systems disclosed herein can be between any two stakeholders in the system of reference, such as between humans and humans, humans and machines, and machines and machines.

In a preferred embodiment, the collaboration platform for delivering health services provides for an integrated messaging system whereby sender of a message could be prompted with suggested messages, content for review, content for appending to the message, and alternate communication channels for more effective communication based on contextual parameters including but not limited to recipient's profile, recipient's replying tendencies, recipient's availability status, the topic of the message, the message being composed, the sender's preferences, the sender's communication style, and the time of the day message is being composed, among others.

In a preferred embodiment, based on the topic of message, the message content selected by the sender and previous history of interactions involving the recipient, the platform may suggest one or more appropriate moods of the recipient that may be suitable for receiving a message, and associated timeslots. In certain embodiments, the sender chooses to send the message targeting a specific mood of the recipient. The sender may also choose a specific timeslot associated with the mood of choice to send the message. Based on the selection of the sender, the platform schedules the message to be sent at the first instant, the sending criteria matches.

When a timeslot is selected, platform sends message at the selected timeslot. In some embodiments, the platform may delay sending of the message if there is information that the mood of the recipient does not match the desired mood at the time of delivery. In some embodiments, the platform may try delivering the message at another suitable timeslot based on mood and time analysis. In some other embodiments, the platform may notify the sender of the delivery failure.

When a timeslot is not selected, the platform can send the message at the first instant it can match the mood of the recipient with the desired mood at the time of delivery.

In an embodiment, apart from using contextual information, a platform deployment for service delivery may be configured with rules using a rule engine with platform specific rules to be processed to suggest and determine effective messages. Rules may be tied to different types of entities including but not limited to documents (flyers, shared documents, communication attachments etc.), users (doctors, nurses, patients, social workers, etc.), communication channels, organizations (hospitals, clinics, insurance companies etc.), and so on. Also, rules may be relating to access control, routing of workflow for different types of users and processes, user preferences relating to communication on the platform including but not limited to days of week and time of day preferences, communication channel preferences, and so on.

The rules may be generic rules that apply to all forms of communication channels available on the platform, and the rules may be specific to the type of one or more communication channels identified as part of the rule. In an example, a rule may state that all communications related to a particular topic should be encouraged on the instant messenger communication channel. Based on such a rule, the platform can suggest the users to use the instant messenger communication channel whenever a user tries to communicate a message pertaining to the relevant topic. These rules may help the platform determine applicability and efficacy of a particular communication channel for a particular conversation.

Further, rules may be specific to a type of users on the platform, or an identified group of users on the platform. For example, in a healthcare service delivery system, a rule may be defined for Nurses in general or a specific group of Nurses. And, such a rule may be used to define the kind of communication channels that the Nurses can use, the type of users that they can communicate with, preferred communication channels to use to communicate with the Nurses and so on. In a preferred embodiment, various types of users on the platform are defined as roles. Each role may have sub-roles associated with. For example, a role such as Nurse may have a sub-role associated with, such a Junior Nurse and so on.

Furthermore, rules may be relating to security settings relating to all users on the platform or an identified type of users or even an identified group of users. For example, a data access rule may be created for data relating to patients and their interactions on the platform that is more stringent where a group of authorized users on the platform are only given access to the patient data. And, another access rule may be created for certain class documents that pertain to public health issues where access to such information is unrestricted due to the need for disseminating such information to as many people as possible.

The rules in combination with the contextual analysis ensure that the right users have access to the right information, users use appropriate communication channels to communication with other users on the platform, and so on. For example, when a user initiates, for example, a discussion forum posting, the platform may determine that instant chat conversation would be more beneficial or warranted for effective conversation and to reach desired results in a timely manner, based on context based content and the associated rules.

In another embodiment, the platform can enable a rewarding system. For example, the platform could leverage complements as a rewarding mechanism. In case of complementing recipients, the platform can enable users by helping them by showing suggestions to post a compliment, track number of compliments, and how best to complement based on user specific parameters, among others. A ranking system based on the principles of Bayesian probability, context-tree weighting algorithm, and adaptive modeling algorithm together or part of it could be used to determine what the best way to complement somebody is. For example, when using Bayesian probability based algorithm rank messages for appropriateness, a message may be analyzed and success of the message in eliciting the desired response from recipient may be predicted based on probabilities obtained from previous similar messages sent. All the responses from similar user characteristics using similar communication channels can be plotted. Approval scores for the response can be calculated based on likes, user input and other parameters. Assessment of probability of a response being successful (meaning obtaining desired response from the receiver of a message) may be done based on prior probabilities and likelihood of success of a message.

Prior probabilities may be established using the following:

Probability of Positive outcome=Number of positive outcomes/Total Number of Outcomes Probability of Negative outcome=Number of negative outcomes/Total Number of Outcomes And, likelihood of success of a message may arrived at using the following:

Likelihood of $X$ given positive outcomes=Number of positive responses close to $X$/(Total number of positive responses/Positive outcomes)

Likelihood of $X$ given negative outcomes=Number of negative responses in the vicinity of $X$/(Total number of negative responses/Negative outcomes)

In the Bayesian analysis, the final classification is produced by combining both the prior probability and the likelihood, to form a posterior probability using the so-called Bayes' rule, according to the following:

Posterior Probability of $X$ being positive outcome=Prior Probability of positive outcome× Likelihood of $X$ given positive outcomes Posterior Probability of $X$ being negative outcome=Prior Probability of negative outcome×Likelihood of $X$ given negative outcomes The use of a particular algorithm is configurable in the platform. Such a system to encourage rewarding mechanisms like complements may be applicable for but not limited to process flows in healthcare service delivery such as system of care, and hospitality industry, where appreciation for job well done have direct impact and correlation with improving quality of services delivered.

In another embodiment, the platform can enable a message feed in which all communications across different communication channels on the platform are brought together. A message feed can different for different users, and groups/teams on the platform. For example, a message feed for a group/team may show messages relating to all activities for that group/team, including messages between users, documents shared, and so on. For example, a message feed may bring together communications from channels such as chat for instant messaging and blogging to provide a holistic picture for any given user. As an example, if a user X on the platform had conversation with user Y and they are both part of a team or a group configured on the platform, relevant chat transcripts together with blogging information for instance can be shown in a message feed corresponding to the message of user Y being composes for the group/team. Appropriate security privileges are taken into account regarding who can see what message. For example, if a type of communication is only accessible by two users on the platform, even though such a communication might have happened between two users in a group, the message will be visible on the message feed for only to those two users of the group and not others. Further, users may be able to filter content visible to them on message feed based on specific types of communication, based on keywords, based on specific users or groups involved in the conversation and so on. Message feed enables users to connect the dots around a conversation more easily and not miss out on contextual content when interpreting specific information. For example, a care giver on a health care service delivery platform may be able to find all conversations with a particular patient or another care giver to understand the nature of discussions and treatment that has been done in the past.

Blogging, Polling, chat, forums, mail, document exchange, content feeds, communication with external applications, etc are examples of communication mechanisms that can be enabled on the platform. Information from all such mechanisms may be brought together for providing a holistic view on a message feed.

In another embodiment, the platform provides automatic parsing, and placement of relevant information for access by various stakeholders on the platform. For example, documents tagged to be read, are parsed for information. The platform can reach data from files, postings and other content sources on the platform, and run specific business logic to push out the results in the desired format. For example, a free text event discussion may be converted into a calendar event for a user. In case of system of care implementation it may include parsing of Minutes of Meeting document/Strength & Weakness document and other additional types of documents, and taking appropriate actions like posting messages to members of the meeting with notes, submit information on a bulletin board, compare with a previous version and highlight changes in the newer version of the document, and so on, based on the information read from those documents. This would make the process less error prone, save precious time of stakeholders to input the information as well make information available in a timely manner to name a few.

Referring now to the drawings, and more particularly to FIGS. 1 through 8, where similar reference characters denote corresponding features consistently throughout the figures, there are shown embodiments.

FIG. 1 illustrates an example environment where a collaboration platform is deployed and accessed through network. The collaboration platform 102 is accessed by a plurality of users using various electronic devices 114*a-c* connected through a communication network 112. The platform 102 includes a user interface layer 104 to provide user interface functionalities for the collaboration platform 102. Further, the collaboration platform 102 includes application components 106. Furthermore, the application components 106 are connected to a database 108 and external applications through external application connectors 110.

In a preferred embodiment, the communication network 112 is a Wide Area Network (WAN) like the Internet or telecommunication networks. Access to the application components may also be enabled through other network mechanisms including but not limited to Personal Area Networks (PANs), Local Area Networks (LANs), Campus Area Networks (CANs), or Metropolitan Area Networks (MANs). The type of network employed and the reach provided depends on the type of the enterprise that is deploying the platform, the needs of the enterprise, and the distributed nature of the enterprise among other parameters. Therefore, in a various embodiments, the platform components may be distributed across multiple computing servers located at a single location or multiple locations.

In an embodiment, the database 108 is an internal database tightly coupled to the application components 106. In other embodiments, the database is an independent service running on a same computing machine, or a different machine being accessible over a network such as the communication network 112 or otherwise. The database may be a relational SQL database, Operational Database, text database or No-SQL database and/or combination thereof. In some embodiments database may be a single instance running on a single machine. In some other embodiments, there could be a cluster of databases running in multiple locations, each updating each other using a master-slave configuration or otherwise.

The external application connectors 110 can include but are not limited to connectors providing integration with social and CRM applications such as FACEBOOK, TWITTER, YOUTUBE, SAP, SALESFORCE and the like.

In an embodiment, the external application connectors also integrate the platform with healthcare devices, programs, machines and systems such as Electronic Health Record (EHR), Electronic Medical Record (EMR), medical devices including Internet of Things (IoT) devices, and so on. In various embodiments, data can be retrieved from external applications and relevant connected devices to add/update user profile and behavior information.

Figure 2:
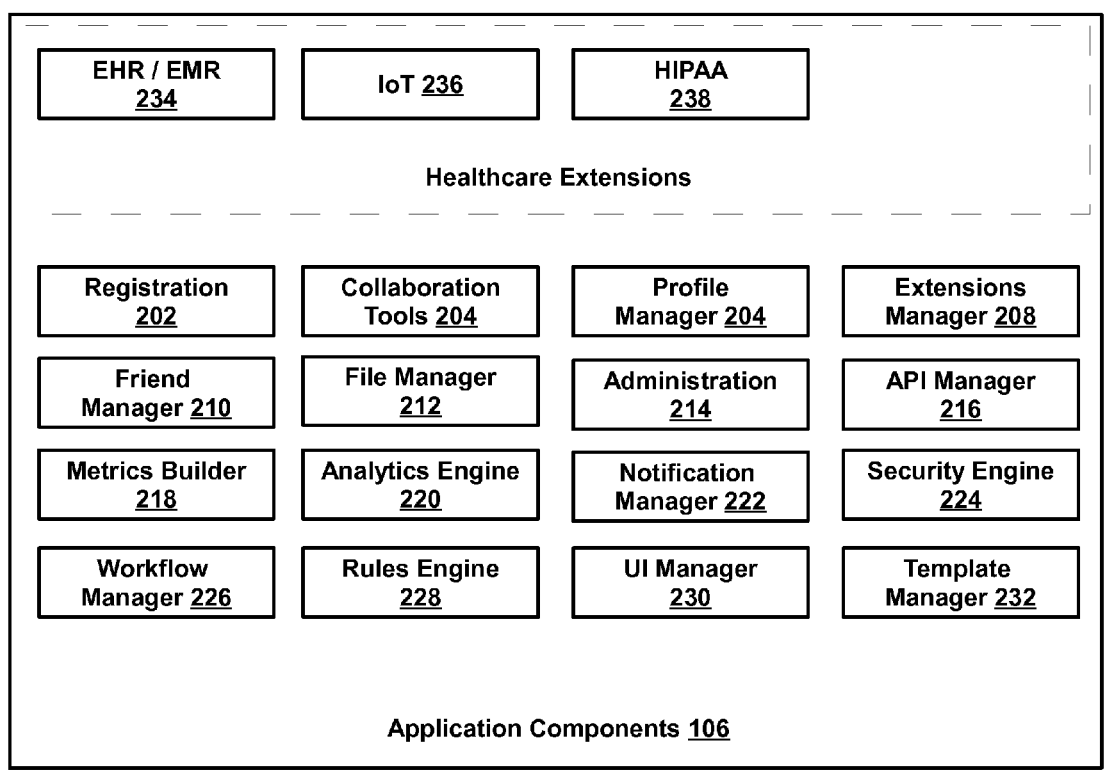
FIG. 2 depicts the various application components as part of the platform, according to an embodiment herein.

FIG. 2 shows the application components. The functionalities of each of the components are described herein.

The registration component 202 is used to obtain initial information on user profile. Fields and process required for registration may differ based on the user or platform role. Information obtained during registration process is stored in the database which is used for deriving of contextual information.

The collaboration tools 204 are used during collaboration between individuals, processes, systems and machines. In an example, the collaboration tools may include but are not limited to chat, message feed, forums, blogs, communications between IOT (Internet of Things), micro-blogging, Document Management, Task Management, Calendar, emails, comments, images, videos, and interactions between internal and external EHR and/or EMR systems.

The profile manager 204 is used for managing user profile information in the collaboration platform. If the user profile information is not complete, then the profile management works with notification manager component to publish notifications or reminders to fill missing information from time to time.

User can be invited into collaboration platform through multiple ways. Through a friend manager 210, user can be invited into the collaboration platform as a friend of an individual, or a group/team.

Through a file manager 212, document sharing among teams, individuals, system and machines is facilitated. In an embodiment, the file manager 212 allows multiple feature set including check in and checkout functionality to ensure that documents are not overwritten, assignment of document access privileges, and so on.

In an embodiment, an analyzer (not shown) could use file manager 212 component to derive a file retrieval link that could be included as a reference under published suggestive dataset.

An administration component 214 is used to manage users, roles, processes, rules, workflows, governance, user posted content, and platform content.

An API manager 216 is used in conjunction with extension manager to pull and publish content from external sources.

A metrics builder 218 manages the type of metrics to capture during various transactions and processes in the collaboration platform. It is used by analytical engine to build reports. Metrics around accuracy of suggestive dataset is managed by the metrics builder component and leveraged by an analytics engine to build comprehensive reports.

The analytics engine 220 is used to build reports on various user transaction and platform processes and provide relevant insights. Different types of analytic reports could be created based on configured algorithm.

A notification manager 222 is responsible for generating notification across the collaboration platform. As an example, the notification manager may provide notifications for requesting a user to populate critical items on their profile, asking the user about the mood from time to time to inform the user about availability of suggestive data set in case it cannot be made available in real-time.

A security engine component 224 is responsible for ensuring that standards and compliance are effectively enforced. In case there is any lapse, authorities are informed in a timely manner. In an embodiment, the security component determines what results should be discarded from the analyzer processed data set, which data fields to be anonymized and what should be formatting of published results for the user.

The workflow manager 226 creates multiple workflows to implement facilitate processes and rules. Some of the actors in the workflow may include processes, humans/people, machines and systems. The rules engine is used to build rules which would be invoked in a workflow.

The rules engine 228 would be used by the collaboration platform to decide which flow or path to take based on specific input. For example, the rules engine would help in selection of relevant algorithm based on the context information; laying out process around how to retrieve relevant information from repository and so on. Each user role may use different set of templates.

The user interface (UI) manager 230 interacts with the user interface layer to construct data models and user interface details for the user interface layer 104 to render data on a display screen. The UI manager 230 also performs marshaling and un-marshaling of data to support event driven calls from the user interface layer 104. The UI manager 230 may also push data to the user interface layer based on notifications to be delivered by the notification manager 222.

The template manager 232 is used for creating those templates and managing its assignments across user set. In an embodiment, the template manager 232 component is used to create templates for designing user input screen for mood data collection, showing contextual information based on user preferences and security engine guidelines. Templates may be attached to workflows based on configuration provided in the workflow manager 226. And, templates may be invoked based on rules from the rule engine 228 as attached to specific workflows configured in the workflow manager 226.

An extension manager 208 is used for connecting with configurable external components to extend the capabilities of the platform. For example, a generic platform may be made specific for Healthcare services delivery by adding healthcare related components in a configurable manner. The extension manager 208 allows for adding additional components such the module the healthcare extension components depicted.

The healthcare extensions include EHR/EMR 234 integration component, IoT 236 integration component, and a Health Insurance Portability and Accountability Act compliance component (HIPAA) 238 that ensures that the platform is complying with HIPAA regulation.

The platform allows for interactions between EHR/EMR component 234 and external EHR/EMR systems for data updation and synchronization. The data managed by EHR/EMR component 234 are used to build holistic information of user profile to ensure that the user characteristics are correctly mapped. For example in case of Behavioral Health (Mental Health, Substance Abuse and Development Services) it may include information on Consumer's Crisis Plan, Strength & Success document to name a few that enables platform/system to create more holistic picture such as what to do when Crisis happens, what interventions to undertake, etc. Data is pushed and pulled using EHR/EMR 234 component as part of the process flow. Relevant data would be displayed in suggestive text section based on these inputs. Data managed by EHR/EMR 234 component may include user diagnosis information, medical history and so on.

Similarly, the platform allows for an Internet of Things (IoT) integration component 236 to connect with various external IoT devices based on available standard connection mechanisms, particularly those relating to patient monitoring and vital data collection. IoT integration component 236 may obtain patient and care giver information from external devices and update user profile information on the platform for further use and analysis.

The primary goal of the HIPAA regulation is to make it easier for people to keep health insurance, protect the confidentiality and security of healthcare information and help the healthcare industry to control administrative costs. The platform provides built-in controls such as encryption, and other data and communication security procedures to ensure that user PHI and electronic protected health information (ePHI) is protected. In an embodiment, data is anonymized to ensure that user ePHI or PHI is obfuscated during deriving of contextual information. In addition, other components have also been created in the healthcare extensions including PCI (Payment transaction), SSAE 16, ISO 27001 certification for datacenter and the like which is required for Healthcare transactions and data communications and reporting. HIPAA compliance component 238 ensures such compliance for all relevant data managed by the platform.

Figure 3:
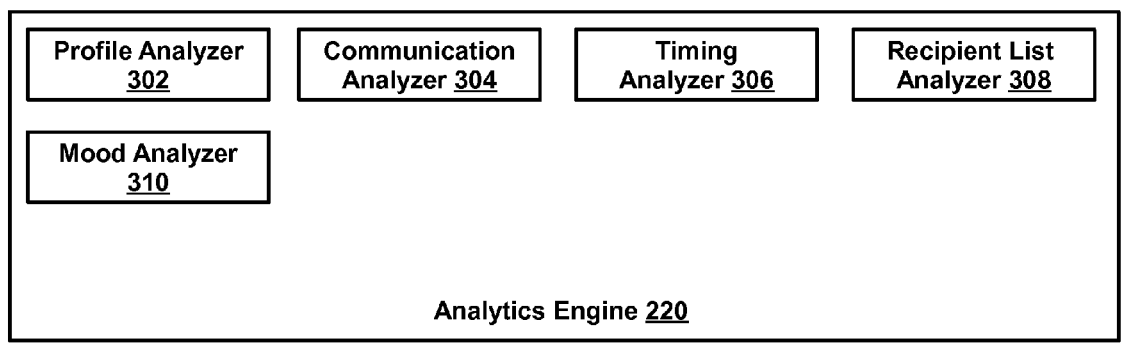
FIG. 3 depicts various sub-components of analytics engine of the platform, according to an embodiment herein.

FIG. 3 depicts the various sub-components of the analytics engine 220, such as a profile analyzer 302, a communication analyzer 304, a timing analyzer 306, a recipient list analyzer 308, and a mood analyzer 310. The functionality of the components is described herein.

In an embodiment, the profile analyzer 302 component analyzes user profiles based on parameters such as age, education, platform role (example: Social Worker, Provider, Natural Support, Authorized Representative, Parents, consumer (Youth and Adult), Super admin, admin, Care coordinator, Policy Maker, Supervisor), location, health index and the like. Some of the factors that dictate user's health index are listed below.

a) How many chronic diseases and its state?
b) How many average doctor visit in a typical year
c) Are they overweight?
d) Any hereditary diseases from their ancestors?
e) Life expectancy
f) Did their ancestors die because of chronic diseases like cancer, etc?
g) Disability and if so of what type?
h) How many times did they have Mental Health crisis episode last year?
i) On average how much time it took to resolve an individual crisis episode?
j) Diagnosis of Mental Health (MH) condition?

Data about the above mentioned parameters are stored in the repository so that the profile analyzer 302 optimally retrieves data.

Each platform user communication style is stored in data repository. The communication analyzer 304 analyzes communications to find if they resemble in communication style, content, and so on. In order to derive communication style of the user, his/her communication style on the platform is matched with data store to identify which style he/she belongs to.

In an embodiment, the communication style of the user includes but is not limited to an aggressive communication, a Passive-Aggressive Communication, an Assertive Communication, a Passive Communication.

Some of the statements suggestive of user with aggressive communication expresses are given below:

a) The other person is inferior, wrong, and not worth anything
b) The problem is the other person's fault
c) They are superior and right
d) They will get their way regardless of the consequences
e) They are entitled, and that the other person 'owes' them.

A user with the Passive-Aggressive communication frequently mutters to herself instead of confronting another person. They often smile at others, even though they are angry, use subtle sabotage, or speak with sarcasm.

When passive-aggressive individuals communicate, they may send messages like the following:

α) "I'm weak and resentful, so I sabotage, frustrate, and disrupt."
β) "I'm powerless to deal with you head on so I must use Guerrilla warfare."
χ) "I will appear cooperative, but I'm not."

Assertive communication user clearly states one's opinions and feelings, and firmly advocates for his or her rights and needs without violating the rights of others. They are in control of their emotions and speak in calm and clear tones. They are good listeners, maintain good eye contact and create a respectful environment for others, and do not allow others to abuse or manipulate them. When assertive people communicate with others, they may send the messages like:

a) "I am confident about who I am."
b) "I cannot control others, but I control myself."
c) "I speak clearly, honestly, and to the point."
d) "I know I have choices in my life, and I consider my options. I am fully responsible for my own happiness."
e) "We are equally entitled to express ourselves respectfully to one another."

Passive communication avoids expressing opinions or feelings, protecting one's rights, and identifying or meeting one's needs. When passive people talk, they may convey messages like the following:

a) "I'm unable to stand up for my rights."
b) "I don't know what my rights are."
c) "I get stepped on by everyone."
d) "I'm weak and unable to take care of myself."
e) "People never consider my feelings."

Reasonable size sample data size is used of message composition to ensure that communication style is effectively calculated. For every 90 days or a specific configurable period, this evaluation process for communication style is repeated.

The timing analyzer 306 maps the mood of a user on the platform and during timeslots, and stores the information accordingly.

In an example, 24 hour slot is broken down into 4 hour timeslot as 12:00 am-6:00 am, 6:00 am-12:00 pm, 12:00 pm-6:00 pm, and 6:00 pm-12:00 am. In some embodiments, timeslots may be configurable by the administrators. For example, at the time of setting up a new deployment of the platform, administrators of the platform may choose to have a more refined 6 timeslots during a 24 hour period.

Based on the type of posting a user does using reasonable dataset, the mood analyzer 310 can identify the mood of user during a given timeslot. The moods captured by the platform may be one of the moods, but not limited to, as listed in Table 1. The mood of a user may be assessed by the words as used by the user in their communications, or by using known techniques in textual analysis such as Natural Language Processing (NLP). Mood results from above approach may be augmented with data retrieved from IoT devices such as medical devices. For example, person who is angry at times has a higher blood pressure than their normal rate and their chances of heart attack are much higher. This and other rules which are configured allow system & platform to figure out a pattern about the user mood at particular timeslot if this data is available. Medical device data may be used in conjunction with identifying mood of the user by their use of words or known techniques in textual analysis or combination thereof if relevant data/information are available. Data feed through IoT device/s can also be used in solo for mood analysis if other means of data analysis are not available or not configured in the system. In some embodiments IoT devices such as IP phone can be used an extension mechanism to show suggestive text such as to call a caregiver and phone number is attached or linked with the message. User has to click on the message to start the conversation. This may be the only channel for suggestive text or it may be done in combination of suggestive text shown on the platform.

In some embodiments, known packages for analyzing mood based on NLP may be added as an extension component and configured to be used by the mood analyzer 310 for mood categorization.

indication from sender (example, care giver) to send a message along with topic or message to one or more recipients (example, a patient or a specific group of patients). The collaboration platform obtains (504) sender and recipient profile information and aggregate (506) previous history of relevant interactions from multiple sources. Further, the collaboration platform analyzes (508) relevant interactions from multiple sources to determine list of suggested messages using analytics engine. The collaboration platform filters (510) messages using a security engine. Further, the collaboration platform personalizes (512) messages using analysis from the analytic engine. Furthermore, the collaboration platform ranks and assigns color code (514) for messages based on relevancy, based on Bayesian or other appropriate algorithms.

In an embodiment, the profile analyzer 302 analyzes the sender and receiver profile information of the sender and

TABLE 1

| | | | | | | | |
|---|---|---|---|---|---|---|---|
| Accepted | Accomplished | Aggravated | Alone | Amused | Angry | Annoyed | Anxious |
| Apathetic | Ashamed | Awake | Bewildered | Bitchy | Bittersweet | Blah | Blank |
| Blissful | Bored | Bouncy | Calm | Cheerful | Chipper | Cold | Complacent |
| Confused | Content | Cranky | Crappy | Crazy | Crushed | Curious | Cynical |
| Dark | Depressed | Determined | Devious | Dirty | Disappointed | Discontent | Ditzy |
| Dorky | Drained | Drunk | Ecstatic | Energetic | Enraged | Enthralled | Envious |
| Exanimate | Excited | Exhausted | Flirty | Frustrated | Full | Geeky | Giddy |
| Giggly | Gloomy | Good | Grateful | Groggy | Grumpy | Guilty | Happy |
| High | Hopeful | Hot | Hungry | Hyper | Impressed | Indescribable | Indifferent |
| Infuriated | Irate | Irritated | Jealous | Jubilant | Lazy | Lethargic | Listless |
| Lonely | Loved | Mad | Melancholy | Mellow | Mischievous | Moody | Morose |
| Naughty | Nerdy | Numb | Okay | Optimistic | Peaceful | Pessimistic | Pissed off |
| Pleased | Predatory | Quixotic | Recumbent | Refreshed | Rejected | Rejuvenated | Relaxed |
| Relieved | Restless | Rushed | Sad | Satisfied | Shocked | Sick | Silly |
| Sleepy | Smart | Stressed | Surprised | Sympathetic | Thankful | Tired | Touched |
| Uncomfortable | Weird | | | | | | |

When sender or poster is publishing a message, it would be compared with mood information which is stored corresponding to the timeslot, to identify what may be mood of the poster and recipient during timeslot in the question. Based on that data set would be recommended.

For example, the mood of the user in the timeslot 12:00 am-6:00 am is identified as confused and 6:00 pm-12:00 am is identified as sad.

The recipient list analyzer 308 evaluates the characteristics of one or many users to ensure that they see content in the form they would like to see the message. For example, chat conversation may be their preference. They would like to discuss about non-serious aspects before discussing about a serious matter. Further, users may have a tendency to dislike certain words in conversations: hurt, kill, etc. In an embodiment, the recipient list analyzer 308 analyzes content before publishing based on analysis of preferences of recipients of content. The recipients may be recipients of a specific message being sent from another user on the platform, or may be consumers of public information being posted on forums, and message feeds. Therefore, different users on the platform may see the same message on the platform differently based on their unique preferences and behaviors specific to them.

Figure 4:
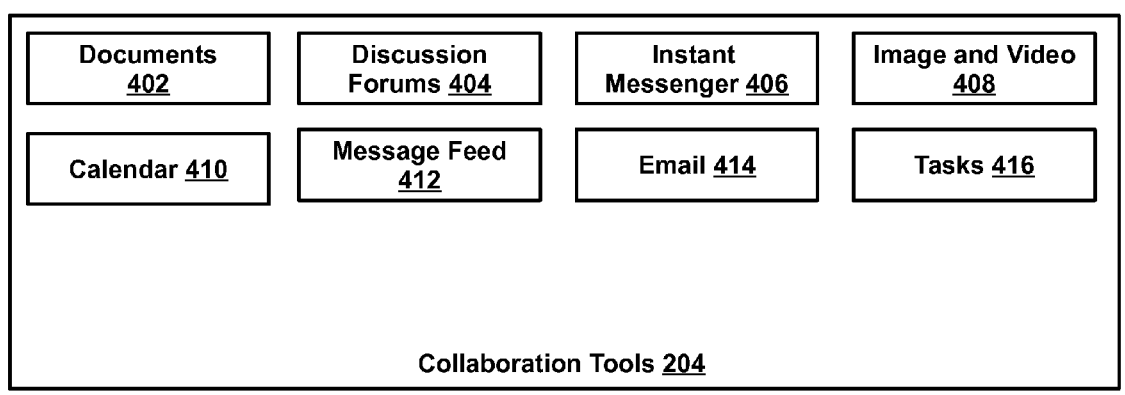
FIG. 4 depicts the various collaboration tools that are part of the platform, according to an embodiment herein.

FIG. 4 depicts some of the collaboration tools that are used during collaboration between individuals, processes, systems and machines includes but are not limited to documents sharing tool 402, discussion forums 404, instant messenger 406, image and video sharing tool 408, message feed 412, Email 414, Tasks 416, and calendar 410.

Figure 5:
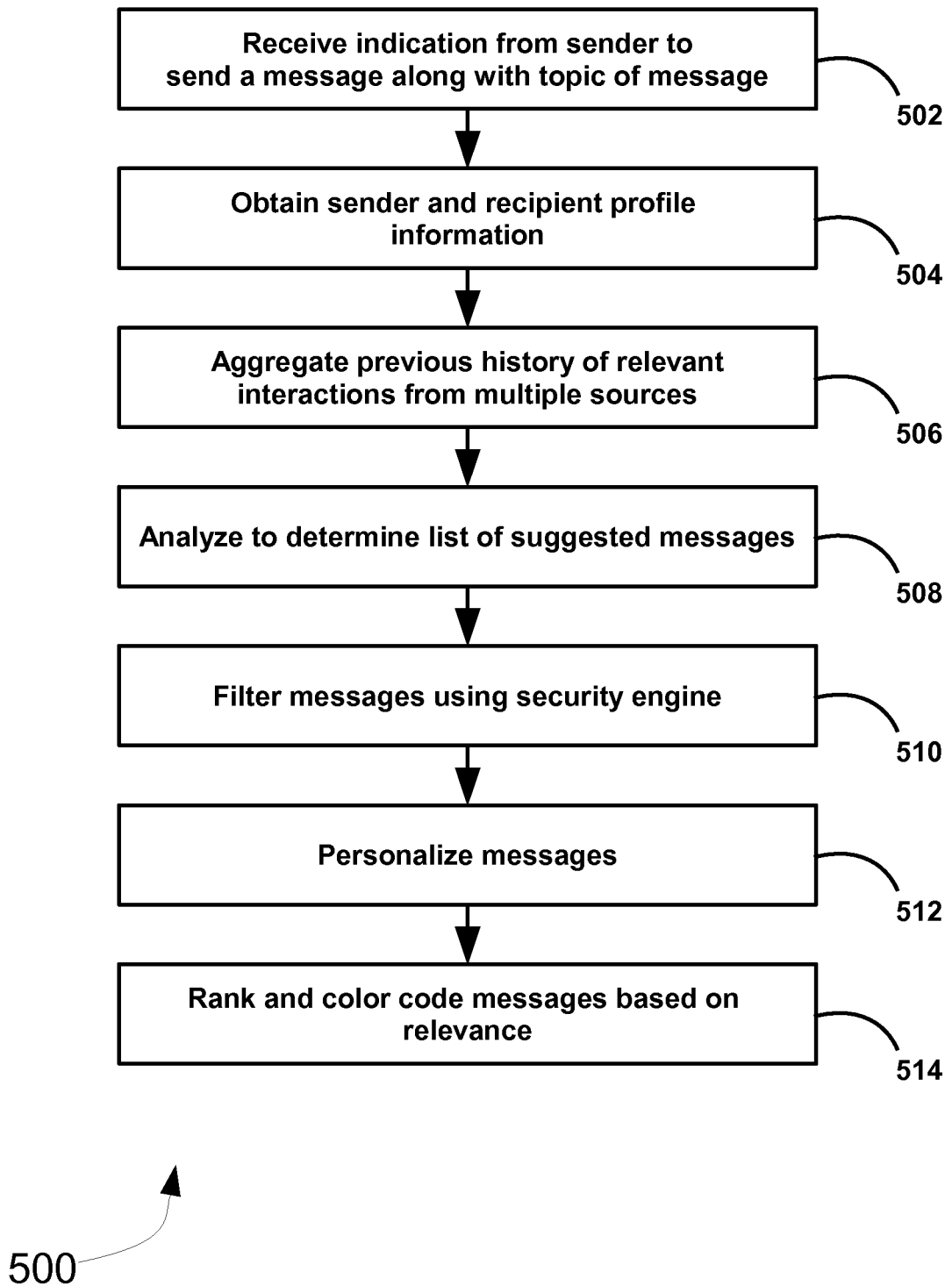
FIG. 5 illustrates a method of communication on the platform, according to an embodiment herein.

FIG. 5 illustrates a method of communication on the platform. Initially, the collaboration platform receives (502)

receiver, and the communication analyzer 304 analyzes the communication preferences, styles, and previous history of communications relevant to the message being sent between any two users on the platform with higher weightage being given to previous communications involving the sender and the receiver. Based on the analysis from profile analyzer 302 and communication analyzer 304, a list of suggested messages may be arrived at. The suggested messages may be anonymized using the security engine, based on security preferences and rules associated with the receiver and the sender. The anonymized messages are further personalized using the recipient list analyzer 308, where for the purposes of displaying messages, the sender is the recipient of the list of messages. The recipient list analyzers 308 analyzing suggested message list to ensure that the sender views the messages that are personalized based on his preferences according to his communication style.

The various actions in method 500 may be performed in the order presented, in a different order or simultaneously. Further, in some embodiments, some actions listed in FIG. 5 may be omitted.

Figure 6:
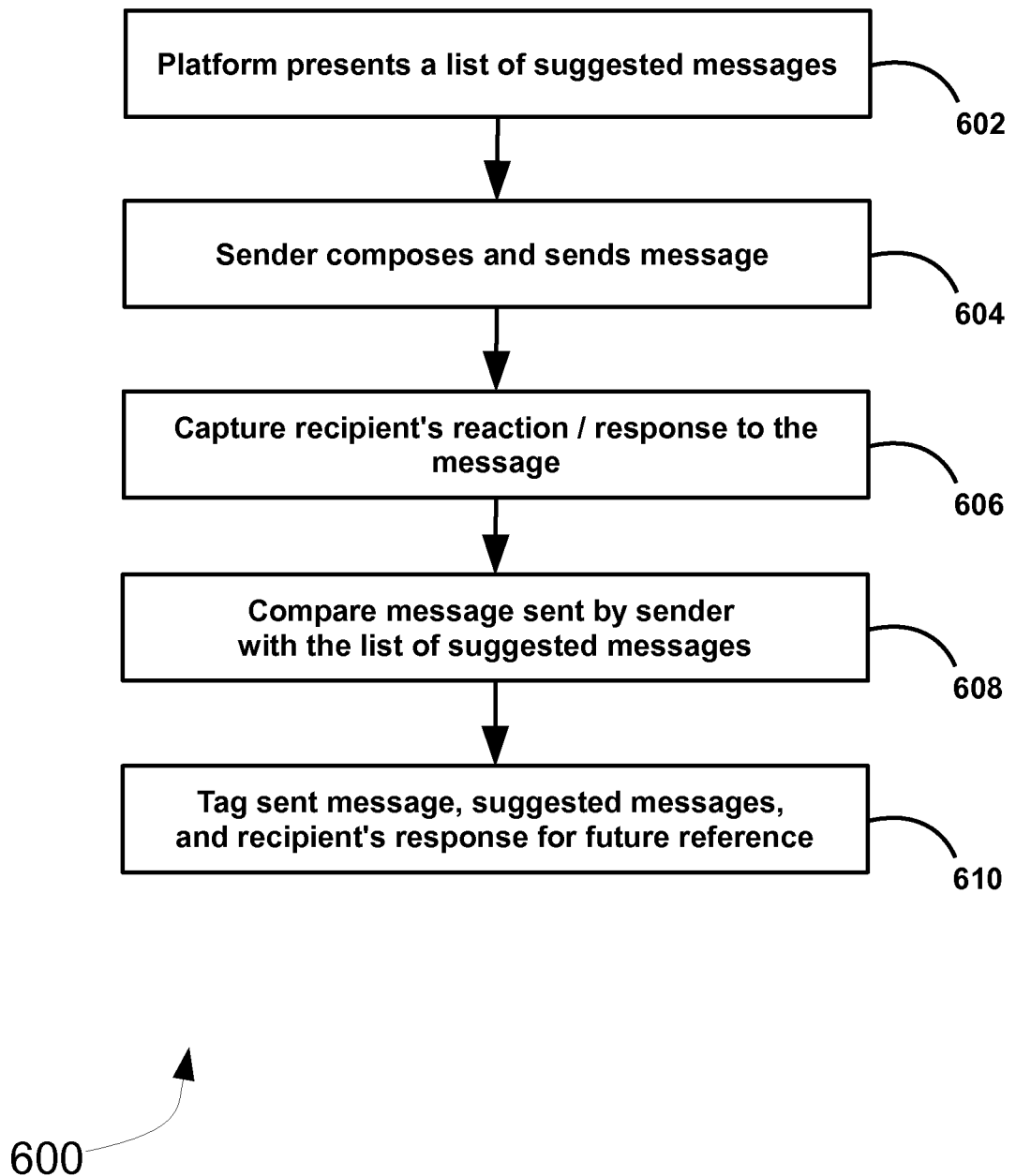
FIG. 6 illustrates a method of storing relevant information from a communication on the platform for future analysis, according to an embodiment herein.

FIG. 6 illustrates a method of storing relevant information from a communication on the platform for future analysis. Initially, the collaboration platform presents (602) list of suggested messages. The sender composes the message and sends (604) the message. Further, the collaboration platform captures (606) recipient's reaction or response to the message and compares (608) message sent by the sender with the list of suggested messages. Furthermore, the collaboration platform tags (610) sent message, suggested messages and recipient's response for future reference.

The various actions in method 600 may be performed in the order presented, in a different order or simultaneously. Further, in some embodiments, some actions listed in FIG. 6 may be omitted.

Figure 7:
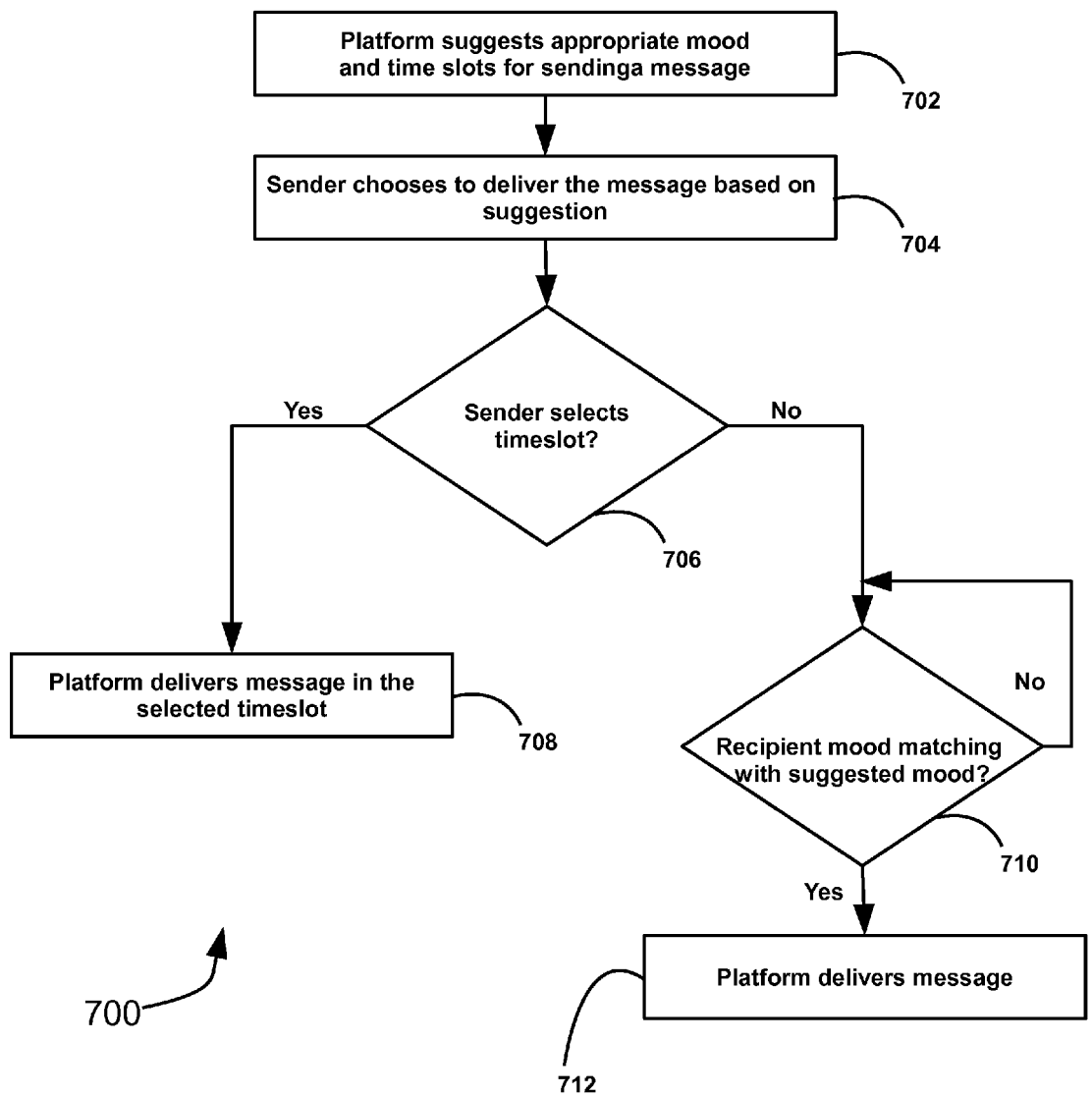
FIG. 7 illustrates a flow diagram for delivering a message based on the suggested mood and associated timeslots depending on the choices made by the sender, according to an embodiment herein.

FIG. 7 illustrates a flow diagram for delivering a message at a later point in time based on the suggested mood and associated timeslots depending on the choices made by the sender, according to an embodiment herein. The platform suggests (702) one or more appropriate moods of the recipient that may be desired at the time of receiving a message by the receiver, and associated timeslots, based on the topic of message, the message content selected by the sender, and previous history of interactions involving the recipient. The sender chooses (704) for the platform to deliver the message to the recipient based on a desired mood selection. The sender may also choose an associated timeslot suggested by the platform. If a timeslot is selected (706) by the sender, the platform schedules delivery of the message in the selected timeslot and sends the message during the timeslot (708). If the sender has not selected a timeslot for a desired mood, the platform matches (710) the mood of the recipient when he is available and delivers (712) the message when the mood matches.

In some embodiments, the platform may notify the sender of delivery failure after certain number of tries or after elapse of a configurable period of time.

Figure 8:

FIG. 8 and FIG. 9 show a message composing screen. FIG. 8 shows the message composing without suggestion views. The message composer provides facility to add a recipient, enter a topic, select category relevant to the message, enter a message, and enter one or more tags to be associated with the message. In various embodiments, apart from suggesting possible messages, the platform may provide suggestions for the other free form entry fields like the fields to enter the recipient, topic of the message, and tags associated with the message.

In helping to enter the recipient, as soon as the sender starts typing, the platform can suggest a list of possible recipient name, based on the starting letters in the first name, last name, display name, short name, and/or username used by the platform to identify a user.

Similarly, in helping the sender with the topic of the message, as the sender starts typing, the platform can display a suggested list of topics based at least on previous topics used by the sender, or topics used by other users on the platform subject to security rules based on results from contextual processing.

Similarly, the platform may also show a list of suggested tags as the sender types in tags. The tags may be relevant to the message composed, or the tags already entered. The tags used by the sender previous for similar or other messages may be suggested by the platform as appropriate.

FIG. 9 shows a message composing screen along with suggestion areas. In an example embodiment, various suggestion areas may appear dynamically on the right of message composing area. However, in various embodiments, the relative position of the display area may be different. As an example, the chat history of the user and the documents are shown along with the composing screen.

For instance, as the user composes the message, platform may associate the content of the message with one or more documents that are accessible to the sender and are relevant to the conversation, and display the list of documents in a document display area as depicted in FIG. 9. For example, a relevant document may be a health information document associated with a prescription drug that the message is about. In such an example scenario, the sender may choose to review the information in the document or even attach the document to the message by choosing relevant menu option by the user interface as appropriate. In another example, a suggested video or image link can be included to the message to aid in enhancing the efficacy of the message. Such content may be used in a healthcare service delivery scenario, where additional content may aid in improving the mood of a recipient where the received message is not so pleasant (example, requesting to take a prescription).

Further, the platform may identify relevant conversations that the sender should be aware of or may find useful to understand the context of interactions with the recipient in relation to the current message before sending the message. Such conversations may be displayed by the platform in a chat conversation area as depicted in FIG. 9.

Furthermore, the platform may also provide actual list of suggested messages like "Hi, How are you?" or "How was tennis game?", depending on the context of the conversation, and preferences/behavior of the recipient as determined by various parameters captured by the platform. Such a suggestion may be displayed in a display area like the ones shown for documents and chat history in FIG. 9.

Also, the platform may also provide suggestions for alternate communication channels that may be used to communicate with the recipient based on a combination sender preferences/behavior and recipient preferences/behavior. Furthermore, the platform may also suggest delivering the message at a different time based on the mood behaviors of the recipient and appropriateness of various moods for the message being composed or selected by the sender.

The embodiments disclosed herein can be implemented through at least one software program running on at least one hardware device and performing network management functions to control the network elements. The network elements shown in FIG. 1 include blocks which can be at least one of a hardware device, or a combination of hardware device and software module.

The embodiments herein disclose an integrated collaboration platform and associated methods and systems for contextual communication. Therefore, it is understood that the scope of the protection is extended to such a program and in addition to a computer readable means having a message therein, such computer readable storage means contain program code means for implementation of one or more steps of the method, when the program runs on a server or mobile device or any suitable programmable device. The method is implemented in a preferred embodiment through or together with a software program organized in several software modules being executed on at least one hardware device. The hardware device can be any kind of device which can be programmed including e.g. any kind of computer like a server or a personal computer, phone, tablet, or the like, or any combination thereof, e.g. one processor and two FPGAs. The device may also include means which could be e.g. hardware means like e.g. an ASIC, or a combination of hardware and software means, e.g. an ASIC and an FPGA, or at least one microprocessor and at least one memory with software modules located therein. Thus, the means are at least one hardware means and at least one software means. The method embodiments described herein could be implemented in pure hardware, for example, by way of logic embedded hardware modules, or partly in hardware and partly in software. Alternatively, the invention may be implemented on different hardware devices, e.g. using a plurality of CPUs.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims as described herein.

I claim:

1. A computer-implemented method for communication between a sender and a receiver on an integrated communication platform, said method comprising:
   receiving an indication from said sender to communicate with said receiver by selecting said receiver as a recipient by a user interface (UI) manager;
   analyzing, using a plurality of analyzers, at least one among topic of communication, profile information of said receiver, communication style of said sender, time of day of communication, previous history of communication with said receiver on said platform by an analytics engine;
   determining a list of one or more suggested messages to send to said receiver by said analytics engine;
   filtering said list of suggested messages by a security engine to eliminate messages based on security preferences associated with profile of said receiver;
   anonymizing content in said filtered list of suggested messages by said security engine based on security preferences associated with profile of said receiver; and
   personalizing said anonymized list of suggested messages by analytics engine based on preferences associated with profile of said sender; and
   presenting said personalized messages by said UI manager.

2. The method in claim 1, wherein said indication from said sender to communicate with said receiver further comprises providing a topic of communication with said receiver.

3. The method in claim 1, wherein said plurality of analyzers include at least one of:
   profile analyzer;
   communication analyzer;
   timing analyzer;
   recipient list analyzer; and
   mood analyzer.

4. The method in claim 1, wherein said profile information of said receiver comprises:
   age;
   category of symptoms;
   whether said receiver has been in a crisis situation;
   the number of times said receiver has been in a crisis situation before;
   characteristics of care team assisting said receiver;
   location;
   records mood information of said receiver;
   tags associated with the person; and
   notes provided by senders.

5. The method in claim 1, wherein analyzing further comprises predicting one or more words that should be avoided in communications with said receiver.

6. The method in claim 1, wherein analyzing further comprises predicting mood of said receiver at said time of day.

7. The method in claim 1, wherein analyzing further comprises predicting a suitable communication style based on communication style of said sender and communication style preferred by said receiver.

8. The method in claim 1, wherein determining a list of one or more suggested messages further comprises predicting mood of said receiver at said time of day for said topic of communication.

9. The method in claim 1, wherein filtering said list of suggested messages by a security engine further comprises:
   analyzing if said sender has access to each message of said list of suggested messages; and
   eliminating one or more messages to which the sender does not have access.

10. The method in claim 1, wherein anonymizing content in said filtered list of suggested messages further comprises obfuscating personal information associated with any individual to which said sender does not have access.

11. The method in claim 1, wherein anonymizing content in said filtered list of suggested messages further comprises obfuscating personal health information associated with any individual.

12. The method in claim 1, said method further comprising presenting a list of suggested documents relevant to said communication for review.

13. The method in claim 1, said method further comprising ranking said personalized message suggestions based on relevance.

14. The method in claim 1, said method further comprising color coding said personalized message suggestions for identification of relevancy of a message to said communication.

15. The method in claim 1, wherein said list of suggested messages include messages between said receiver and one or more senders communicated one or more communication channels on said integrated platform.

16. The method in claim 15, wherein said communication channels include:
   chat message channel;
   message feed channel;
   blogging channel;
   micro-blogging channel;
   email channel;
   discussion forum;
   announcements;
   image and video channel; and
   document sharing channel.

17. The method in claim 1, wherein said method further comprising:
   said sender selecting a desired mood of said recipient at the time of receiving said message based on suggestions presented;
   said sender selecting a timeslot associated with the mood for delivering said message; and
   delivering said message to recipient based at said selected timeslot by notification manager.

18. A collaborative computerized system comprising:
   a non-transitory computer readable medium having program modules to enable a method for communication between a sender and an receiver on an integrated communication platform, said program modules comprising:

analytics engine for analyzing, using a plurality of analyzers, at least one among topic of communication, profile information of said receiver, communication style of said sender, time of day of communication, previous history of communication with said receiver on said platform, determining a list of one or more suggested messages to send to said receiver, and personalizing an anonymized list of suggested messages by analytics engine based on preferences associated with profile of said sender, security engine for filtering said list of suggested messages by a security engine to eliminate messages based on security preferences associated with profile of said receiver, and anonymizing content in said filtered list of suggested messages based on security preferences associated with profile of said associated with profile of said assisted individual, and user interface (UI) manager for receiving an indication from said sender to communicate with said receiver by selecting said receiver as a recipient, and presenting a list of personalized message suggestions to said sender based on an anonymized list of suggested messages; and a processor for executing program instructions from said computer readable medium.

19. The system in claim 18, wherein said plurality of analyzers include at least one of:
profile analyzer;
communication analyzer;
timing analyzer;
recipient list analyzer; and
mood analyzer.

20. The system in claim 18, wherein said profile information of said receiver comprises:

age;
category of symptoms;
whether said receiver has been in a crisis situation;
the number of times said receiver has been in a crisis situation before;
characteristics of care team assisting said receiver;
location;
records mood information of said receiver;
tags associated with the person; and
notes provided by assisting senders.

21. The system in claim 18, wherein said list of suggested messages include messages between said receiver and one or more senders communicated one or more communication channels on said integrated platform.

22. The system in claim 21, wherein said communication channels include:
chat message channel;
message feed channel;
blogging channel;
micro-blogging channel;
email channel;
discussion forum;
announcements;
image and video channel; and
document sharing channel.

23. The system as in claim 18, wherein said system further comprises:
Electronic Health Record (HER) and Electronic Medical Record (EMR) component to integrate with external EHR and EMR exchanges to obtain at least patient health and medical records information; and
Internet of Things (IoT) component to integrate with external IoT devices to obtain patient vital information for further analysis.

* * * * *